(12) United States Patent
Parker (10) Patent No.: US 8,978,265 B2
(45) Date of Patent: Mar. 17, 2015

(54) BANDAGE/DIAPER AERATION DEVICE

(71) Applicant: Rashendz, Inc., Saint Petersburg, FL (US)

(72) Inventor: Nigel Parker, Tampa, FL (US)

(73) Assignee: Rashendz, Inc., Saint Petersburg, FL (US)

( * ) Notice: Subject to any disclaimer, the term of this patent is extended or adjusted under 35 U.S.C. 154(b) by 0 days.

(21) Appl. No.: 14/186,659

(22) Filed: Feb. 21, 2014

(65) Prior Publication Data

US 2014/0317950 A1    Oct. 30, 2014

Related U.S. Application Data

(60) Provisional application No. 61/817,343, filed on Apr. 30, 2013.

(51) Int. Cl.
*F26B 25/18* (2006.01)
*A47K 10/00* (2006.01)

(52) U.S. Cl.
CPC ..................................... *A47K 10/00* (2013.01)
USPC ................................ 34/92; 604/317; 604/320

(58) Field of Classification Search
CPC .............................. F26B 25/18; F26B 25/185
USPC ...................... 34/92, 239; 604/317, 320, 327
See application file for complete search history.

(56) References Cited

U.S. PATENT DOCUMENTS

| | | |
|---|---|---|
| 4,608,041 A | 8/1986 | Nielsen |
| 6,216,363 B1 | 4/2001 | Swansen et al. |
| 6,450,995 B1 * | 9/2002 | Prabhakar ................... 604/317 |
| 6,803,496 B2 | 10/2004 | Elder et al. |
| 7,524,315 B2 * | 4/2009 | Blott et al. ................... 604/543 |
| 2002/0087129 A1 | 7/2002 | Di Luccio et al. |

* cited by examiner

*Primary Examiner* — Jiping Lu
(74) *Attorney, Agent, or Firm* — Larson & Larson, P.A.; Frank Liebenow; Patrick Reid (57) ABSTRACT

A bandage/diaper drying device includes a gas inlet and channels formed between two layers of a very thin material (e.g. plastic). A spiral tube is positioned between the two layers to reduce occlusion of the layers and maintain flow of gas from the inlet to vents that are directed to a potential source of moisture. The vents are formed on a peripheral distribution channel that is in fluid communication with the gas inlet. In a preferred embodiment, each vent has a one-way duckbill valve allowing for the flow of gas from the peripheral distribution channel to dry a diaper/bandage in which the bandage/diaper drying system is mounted. The one-way duckbill valves reduce backflow of foreign matter into the peripheral distribution channel.

18 Claims, 5 Drawing Sheets

BANDAGE/DIAPER AERATION DEVICE

FIELD

This invention relates to the field of maintaining or improving skin health in wearers of absorbent articles such as diapers, bandages, training pants, adult incontinence devices, feminine hygiene products, and the like and more particularly to a system for reducing wetness and moisture in closed environments such as incontinence-garments, diapers, wound covers of any kind, and the like.

BACKGROUND

Several problems occur when an area of skin is left in contact with moisture, heat, urine, and fecal irritants for extended periods of time. Such exposure occurs in diapers and other incontinence garments where bodily excretion provides moisture and irritants. The same exposure occurs beneath bandages and coverings where bodily heat and lack of air circulation increases the moisture and temperature in the vicinity of the wound. The presence of moisture, combined with heat from the body and irritants from excretions, creates a virtual Petri dish for infections which leads to compromise of the epidermis (skin), diaper dermatitis, ulcers, and other diseases, with a variety of secondary and tertiary problems resulting in the deterioration of the quality of patient care.

To capture moisture, diapers and feminine hygiene products are often made using super-absorbent polymers that absorb moisture without drying the patient's skin. Thus, diapers and incontinence garments, once exposed to patients' excretions remain moist, and provide a source of irritant diaper dermatitis for millions of patients each year in the United States alone.

The ability of the above-mentioned products to fully dissipate body-generated moisture is limited by the passive nature of the absorbency technology underlying all diaper and incontinence garments. There is sometimes a separate layer next to the skin, but this layer will never dry until the entire diapers or incontinence garment dries, which will not happen because a low-permeability outer layer keeps moisture from evaporating to protect clothing, etc., from the liquid materials.

What is needed is a device that will accelerate evaporation and drying of the skin in enclosed environments or covered-wound environments, while simultaneously allowing for the application of gaseous oxygen to repaired compromised skin.

SUMMARY

In one embodiment, a bandage/diaper drying system is disclosed including a gas inlet and a gas distribution channel that is in fluid communications with the gas inlet. Within the gas distribution channel is a spiral tube that helps keep the gas distribution channel from occluding from forces of external pressure. A plurality of vents is interfaced to the gas distribution channel. The vents are in fluid communication with the gas distribution channel and communicate gas from the gas distribution channel towards an area of potential moisture, thereby improving drying of the moisture when present.

In another embodiment, a bandage/diaper drying system is disclosed including a gas inlet and a gas distribution channel. The gas distribution channel is in fluid communications with the gas inlet and the gas distribution channel is formed around a spiral tube that helps keep the gas distribution channel from becoming occluded. A plurality of vents are interfaced to the gas distribution channel; each vent is in fluid communication with the gas distribution channel and each vent has a check valve for allowing the flow of gas out of the gas distribution channel and reducing a flow of contaminates into the gas distribution channel. The vents direct the gas towards an area of potential moisture to improve drying of that moisture when present.

In another embodiment, a bandage/diaper drying system is disclosed including a gas inlet having a gas connector for connecting to a supply of gas. A gas distribution channel is in fluid communications with the gas inlet and is formed around a spiral tube. The gas distribution channel has a plurality of vents. Each vent is in fluid communication with the gas distribution channel and each of the vents has a duckbill check valve, allowing the flow of gas out of the gas distribution channel and reducing a flow of contaminates into the gas distribution channel. Gas, under pressure, is connected to the gas connector and flows into the gas distribution channel, through which the gas is distributed to each of the vents and directed towards a source of moisture.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Throughout the description, as examples of uses of the bandage/diaper drying system, a diaper example will be used. This in no way is limiting and the drying system as described is anticipated for use in many different applications such as diapers, bandages, feminine hygiene products, etc. The exemplary components shown enable one skilled in the art to fabricate the bandage/diaper drying system and it is fully anticipated that other arrangements and types of components be used to produce similar bandage/diaper drying systems.

In some uses of the disclosed system, the supply of oxygen provides localized hyperbaric therapeutic effects. Likewise, the disclosed system is also anticipated for use concurrently as a skin drying device and an oxygen delivery device for specialized non-hyperbaric oxygen therapies. Although oxygen is one gas that is delivered to an area within the, for example, diaper or bandage, any gas is anticipated such as air, nitrogen, etc.

Figure 1:
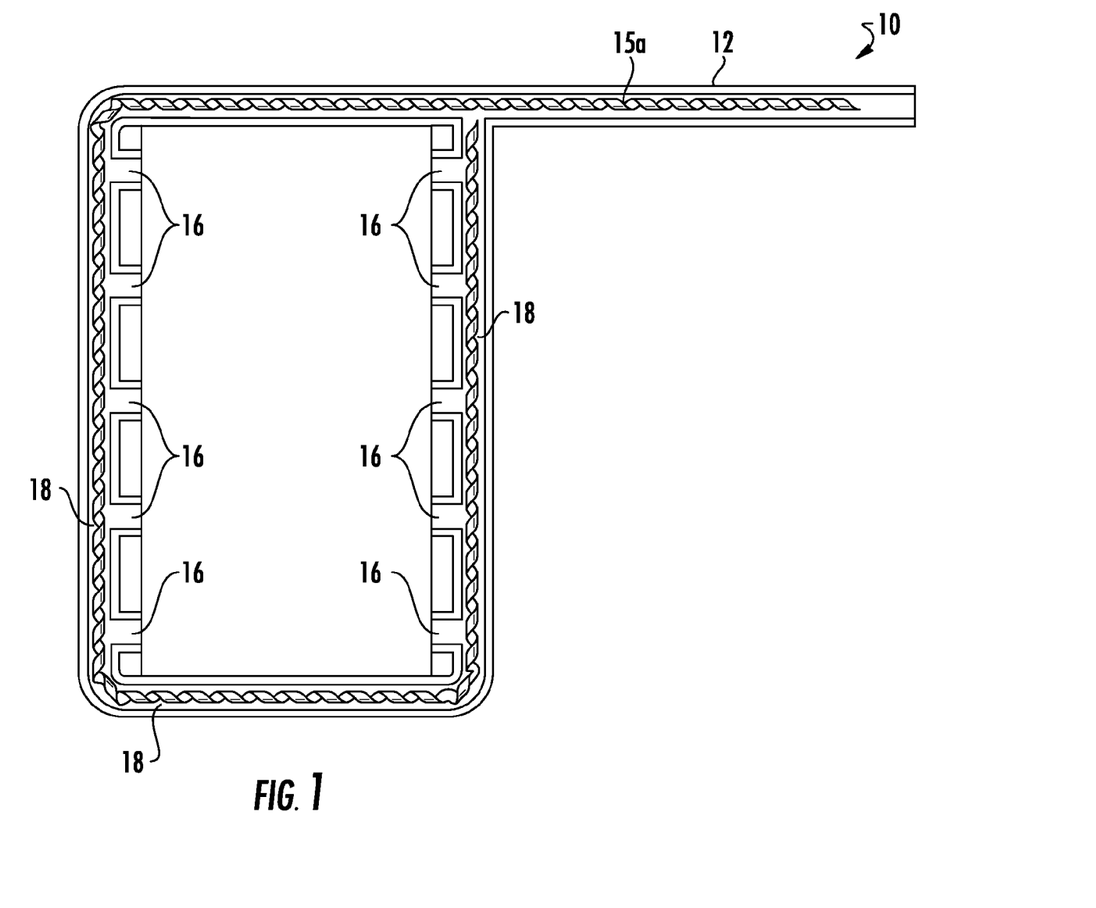
FIG. 1 illustrates a schematic view of a first example of a bandage/diaper drying system.

Referring to FIG. 1, a schematic view of the bandage/diaper drying system 10 is shown without any cover to understand the routing and flow of the gas. In this exemplary bandage/diaper drying system 10, gas such as air, oxygen, etc., is provided at the inlet channel 12, for example, from a hospital oxygen supply port. The gas flows through a gas distribution channel 12/18, from the inlet channel 12 and into the peripheral distribution channel 18, and exits through vents 16, which are positioned and aimed towards a central area, the area in which moisture exposure is expected. Although the central area is shown as being substantially rectangular, any shape is anticipated meeting the needs of a particular application. For example, triangular, circular, or fork-like shapes (e.g. vents on both sides of the fork tines) are equally anticipated.

The exemplary bandage/diaper drying system 10 is installed in or on a bandage/diaper encircling the areas in which moisture is expected. As the gas exits the vents 16, the gas flows through the absorbent material of the bandage/diaper, thereby promoting evaporation of any moisture present in the bandage/diaper.

It is anticipated that, in some embodiments, the exemplary bandage/diaper drying system 10 be integrated into a bandage/diaper or, in other embodiments, as a liner device which adheres to the surface of a bandage/diaper, and is disposed along with replaced diapers/bandage. In the former, the exemplary bandage/diaper drying system 10 is integrated into the bandage/diaper and disposed with the bandage/diaper. In the latter, it is anticipated that the exemplary bandage/diaper drying system 10 may be reusable where clinically allowed, inserted into one bandage/diaper, then removed and inserted into a subsequent bandage/diaper during changing. In such, it is anticipated that a cleaning step be performed.

Figure 7:
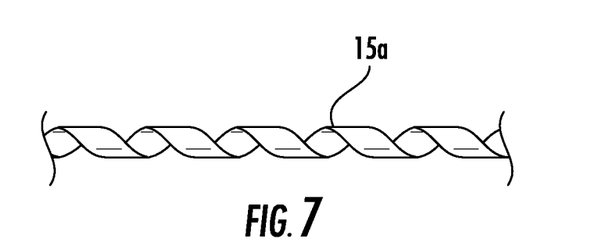
FIG. 7 illustrates a pictorial view of a spiral tube as used in embodiments of the bandage/diaper drying system.

As an example, the gas distribution channel 12/18 is formed of two substantially planar sheets of material 26/28 (see FIG. 4 for an exemplary construction), with a section of spiral tubing 15a running internally through the gas distribution channel 12/18. One desired attribute of the bandage/diaper drying system 10 is minimal thickness. Therefore, the layers 26/28 are preferably made of a very thin sheet of a flexible, non-porous material such as plastic. As one would expect, without a spacing member such as the spiral tubing 15a, pressure forces from a user sitting or the wrapping of a bandage will compress the layers 26/28 and prevent flow of gas. Therefore, a spacing member 15a (the spiral tube 15a as shown in FIG. 7 is preferred but other spacing members are anticipated) maintains air flow while providing a low profile and flexibility. In embodiments using the spiral tube 15a, it is anticipated that the spiral tube 15a be made of any shape-holding, but flexible material such as plastic or thin metal. In embodiments using the spiral tube 15a, the gas flows through the center bore of the spiral tube 15a and exits through the gaps between wrappings of the spiral tube 15a.

As the gas escapes through the gaps between wrappings of the spiral tube 15a, the gas is directed out exit ports or vents 16 and towards the area to be dried (e.g. wet are of a diaper or a wound).

For example, when used in a diaper, moisture is concentrated near the center of the diaper where the source of excretion is located. Having a small distance between the vents 16 and the source of excretion improves delivery of the gas to the moisture to improve drying. The gases are delivered by, for example, turbulent flow to the entire skin covered by the bandage/diaper, from the vents 16 around the source of moisture. The flow of gases such as oxygen expedites drying, enabling effective non-invasive, non-chemical, natural skin drying and dynamic oxygen therapies.

Figure 2:
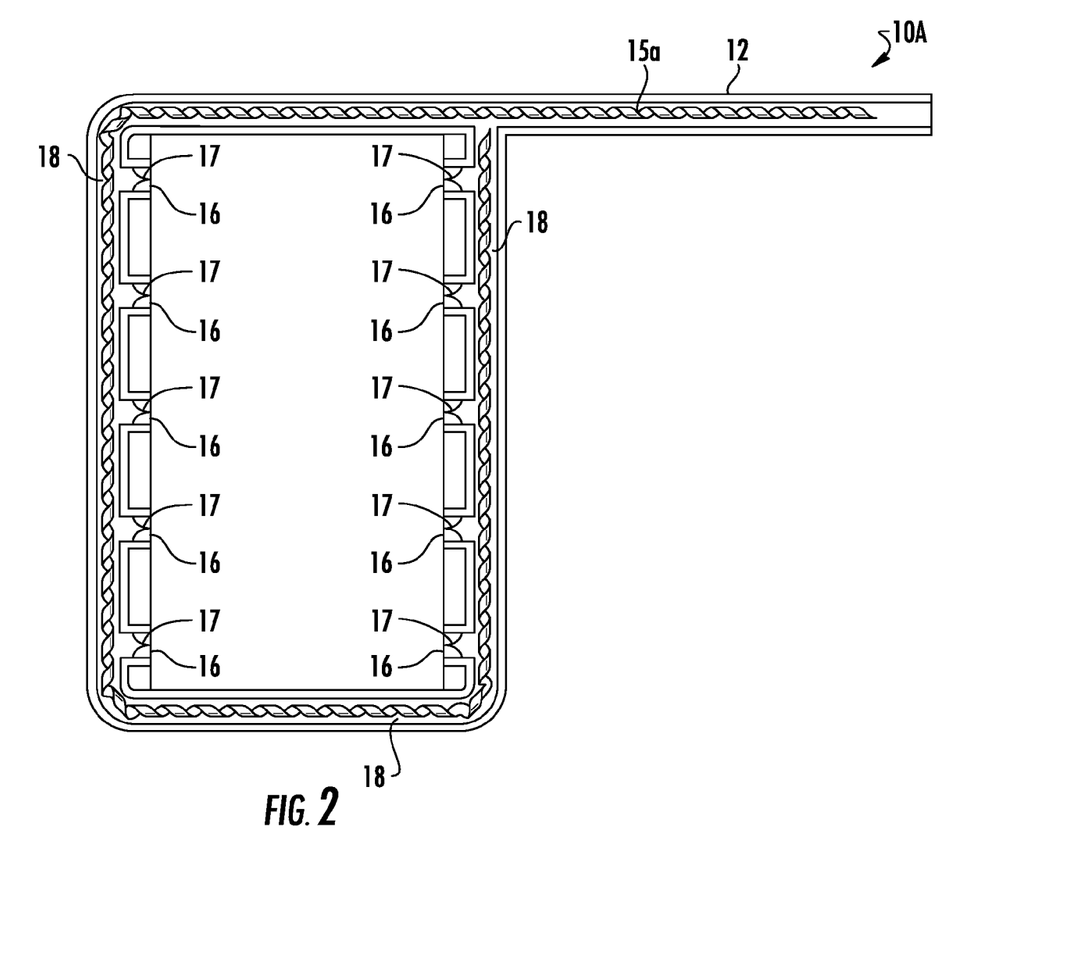
FIG. 2 illustrates a schematic view of a second example of the bandage/diaper drying system.

Referring to FIG. 2, a schematic view of the bandage/diaper drying system 10A is shown, again without any cover to understand the routing and flow of the gas. In this exemplary bandage/diaper drying system 10A, gas such as air, oxygen, etc., is provided at the inlet channel 12, for example, from a hospital oxygen supply port. The gas flows from the inlet channel 12 through the peripheral distribution channel 18 and exits through vents 16 equipped with check valves 17, which are positioned and aimed towards a central area, the area in which moisture exposure is expected. Again, although the central area is shown as being substantially rectangular, any shape is anticipated meeting the needs of a particular application. For example, triangular, circular, or fork-like shapes (e.g. vents on both sides of the fork tines) are equally anticipated.

As the gas exits the vents 16 and the check valves 17 prevent back-flow of liquids or solids into the channel. Therefore, the gas flows into/through the absorbent material of the bandage/diaper, thereby promoting evaporation of any moisture present in the bandage/diaper, but matter from the bandage/diaper is impeded from entering the vents 16 and/or peripheral distribution channel 18 where such materials are not desired. As an example of operation of the check valves 17, if the patient has excreted fecal matter and leans to one side, possibly blocking some air flow out some of the ports 16, the check valves 17 will prevent or at least reduce flow of fecal matter into the vents 16 and/or peripheral distribution channel 18, thereby keeping the vents 16 and peripheral distribution channel 18 free and clear to transport the gases. The preferred check valves are duck-bill valves, as shown, but there is no limitation as to the type of check valve.

It is anticipated that, in some embodiments, the exemplary bandage/diaper drying system 10A be integrated into a bandage/diaper or, in other embodiments, as a liner device which adheres to the surface of a bandage/diaper, and is disposed along with replaced diapers/bandage. In the former, the exemplary bandage/diaper drying system 10A is integrated into the bandage/diaper and disposed with the bandage/diaper. In the latter, it is anticipated that the exemplary bandage/diaper drying system 10A may be reusable where clinically allowed, inserted into one bandage/diaper, then removed and inserted into a subsequent bandage/diaper during changing. In such, it is anticipated that a cleaning step be performed.

As an example, the gas distribution channel 12/18 is formed of two substantially planar sheets of material 26/28 (see FIG. 4 for an exemplary construction), with a section of spiral tubing 15a running internally through the gas distribution channel 12/18. One desired attribute of the bandage/diaper drying system 10 is minimal thickness. Therefore, the layers 26/28 are preferably made of a very thin sheet of a flexible, non-porous material such as plastic. As one would expect, without a spacing member such as the spiral tubing 15a, pressure forces from a user sitting or the wrapping of a bandage will compress the layers 26/28 and prevent flow of gas. Therefore, a spacing member 15a (the spiral tube 15a as shown in FIG. 7 is preferred but other spacing members are anticipated) maintains air flow while providing a low profile and flexibility. In embodiments using the spiral tube 15a, it is anticipated that the spiral tube 15a be made of any shape-holding, but flexible material such as plastic or thin metal. In embodiments using the spiral tube 15a, the gas flows through the center bore of the spiral tube 15a and exits through the gaps between wrappings of the spiral tube 15a.

As the gas escapes through the gaps between wrappings of the spiral tube 15a, the gas exits out exit ports or vents 16 having check valves 17 on each, and the gas is directed towards the area to be dried (e.g. wet are of a diaper or a wound).

For example, when used in a diaper, moisture is concentrated near the center of the diaper where the source of excretion is located. Having a small distance between the vents 16 and the source of excretion helps reduce the likelihood of the vents 16 and valves 17 becoming clogged by certain excretions. The gases are delivered by, for example, turbulent flow to the entire skin covered by the bandage/diaper, from the vents 16 and valves 17 around the source of moisture. The flow of gases such as oxygen expedites drying, enabling effective non-invasive, non-chemical, natural skin drying and dynamic oxygen therapies.

The check valves 17 allow a flow of the gas out from the gas peripheral channel 18 while preventing back-flow of any foreign substances back into the gas distribution channel 16/18. Such back flow is often of a liquid, or soft, pliable solid materials present in the bandage and/or diaper 80/82 (see FIG. 6). It is desirable to prevent contamination of the internal channels (e.g. peripheral distribution channel 18) for various reasons, including: to maintain a clear passage for low-pressure gases from the inlet channel 12, to provide even distribution of the gases to all vents 16 and one-way valves 17, and to reduce contamination from urine, blood, fecal matter, other bodily fluids and solids, etc., to improve reuse of the device and improve cleaning.

Although any one-way valve 17 is anticipated, it is preferred that the one-way valve 17 be a duckbill valve 17. A duckbill valve 17 is a normally-closed, flow-activated valve, made from, for example, rubber or other elastomeric material, and with elastomeric lips shaped similarly to the beak of a duck. The duckbill valves prevent contamination due to back-flow, acting as a low pressure check valves.

The duckbill valves of the exemplary bandage/diaper drying system 10A are, for example, designed to open at a pressure of between two and three psig (pounds per square inch, gauge pressure).

It is anticipated that, in some embodiments, the exemplary bandage/diaper drying system 10A be integrated into a bandage/diaper (e.g. diaper 80/82 in FIG. 6) or, in other embodiments, inserted into a pouch or pocket of a bandage/diaper. In the former, the exemplary bandage/diaper drying system 10A is integrated into the bandage/diaper and disposed with the bandage/diaper. In the latter, it is anticipated that the exemplary bandage/diaper drying system 10A is reusable in some applications inserted into one bandage/diaper, then removed and inserted into a subsequent bandage/diaper during changing.

Figure 3:
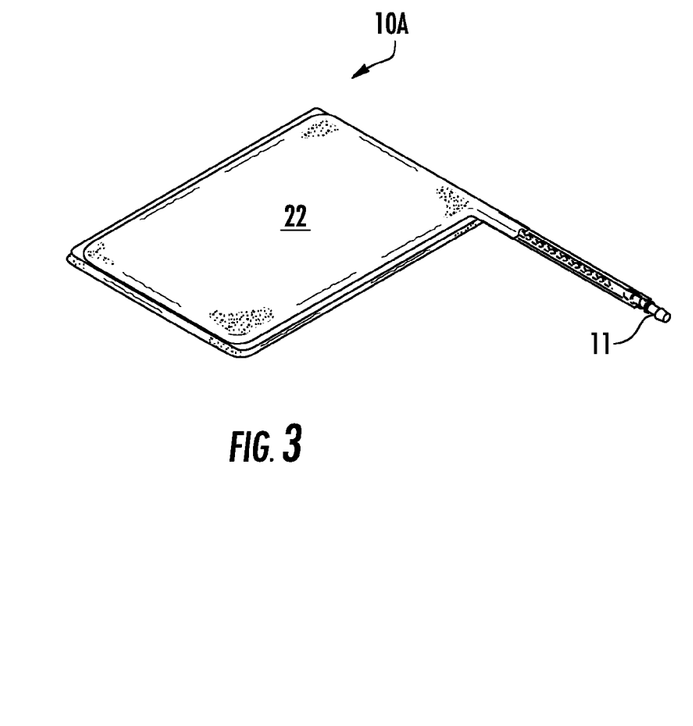
FIG. 3 illustrates a plan view of one exemplary embodiment of the bandage/diaper drying system.
Figure 4:
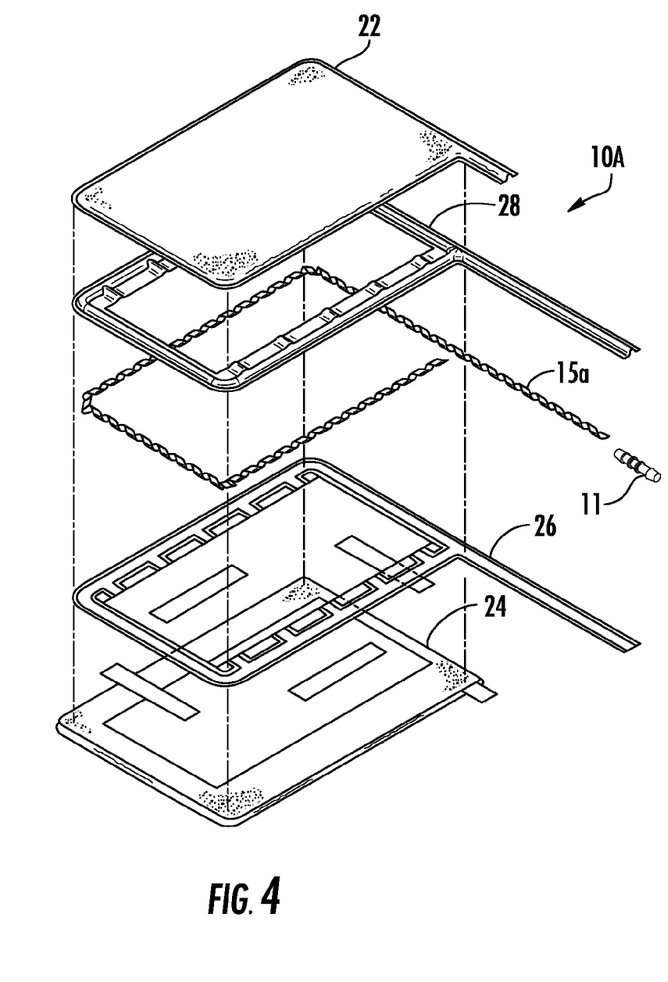
FIG. 4 illustrates an exploded view of the exemplary embodiment of the bandage/diaper drying system.
Figure 5:
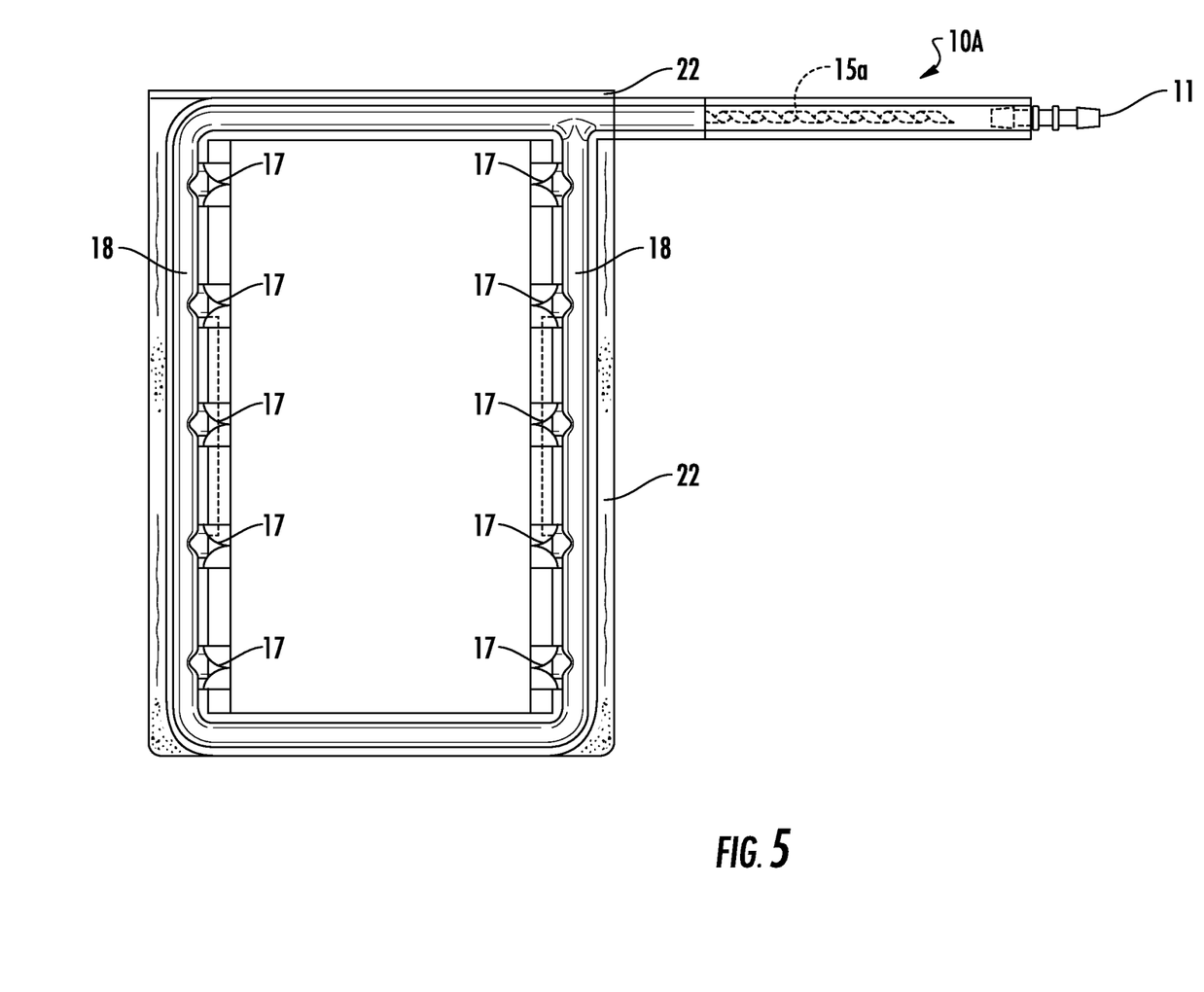
FIG. 5 illustrates a plan view of the exemplary embodiment of the bandage/diaper drying system.

Referring to FIGS. 3-5, views of one exemplary embodiment of the bandage/diaper drying system 10/10A are shown. In the exemplary bandage/diaper drying system 10/10A, a flow of a gas such as air, oxygen, nitrogen, etc., is provided at the inlet 12 through a connector.

In FIG. 4, an exploded view of the layers of an exemplary embodiment is shown. The spiral tube 15a is typically constructing from a long length of flat and narrow material such as plastic that is shaped in a spiral or helix. In a preferred embodiment, the spiral tube 15a is made of a soft polyethylene plastic that will maintain flow of gas through the gas distribution channel 16/18 around the entire perimeter of the bandage/diaper drying system 10/10A, preventing crushing of the gas distribution channels 12/18 by, for example, the weight of a user. Adjacent spirals of the spiral tube 15a maintain separation, allowing the gas to pass through the core of the spiral tube 15a and between adjacent spiral sections of the spiral tube 15a. It is preferred that the spiral tubing 15a is difficult to kink and is flexible. The combination of flexibility and crush-resistance makes the spiral tube 15a ideal for use in a bandage/diaper drying system 10/10A, where patient motion is expected as well as compressive loads.

In a preferred embodiment, the inlet channel 12 connects to a connector 11 for fluid connection to a source of gas (not shown). Some examples of sources of gas are: a hospital gas supply port (e.g. $O_2$ port), an oxygen concentrator, a compressed gas tank (e.g. compressed air), etc. In some embodiments, a small battery operated air pump (not shown) is connected to the bandage/diaper drying system 10/10A, making the bandage/diaper drying system 10/10A portable since the battery operated air pump is easily transportable by the wearer/user. Although one particular connector 11 is shown, there is no limitation on the type or size of connector 11.

Gas enters the bandage/diaper drying system 10/10A through the connector 11 then flows within/around the spiral tube 15a through the inlet channel 12 and then through the peripheral distribution channel 18. As the user of the bandage/diaper drying system 10/10A shifts weight, the spiral tube 15a resists kinking and crushing, thereby maintaining flow of gases from the connector 11 through the peripheral distribution channel 18 and out the vents 16 and check valves 17.

The spiral tube 15a resists kinking while being able to bend as the user moves or pressure is applied to the spiral tube 15a. The construction of the spiral tube 15a provides flow of gases without the need for stiffer tubing that would resist bending and would kink under certain circumstances. The gas flows through and around spiral tube 15a within the inlet channel and the peripheral distribution channel 18 and exits through the vents 16 and one-way valves 17 that are positioned and aimed towards a central area, the area in which moisture exposure is expected. The bandage/diaper drying system 10/10A is installed in or on a bandage/diaper at an area in which moisture is expected. As the gas exits the vents 16 and one-way valves 17, the gas flows by, for example, turbulent flow throughout the diaper covered environment, thereby promoting evaporation of any moisture present on the skin or on the surface of the bandage/diaper.

By distributing the gases from the coupling 11 through the gas distribution channels 12/18 held open by way of a spiral tube 15a, greater resistance to bending, compression, twisting, etc., is achieved, thereby delivering the gases even when under pressure from, for example, the weight of the user sitting upon the bandage/diaper drying system 10/10A.

An exemplary embodiment of the bandage/diaper drying system 10/10A is shown in FIG. 4. The top layer 22 is in direct contact with the skin, and is thus made of a material that is comfortable to the touch. For example, cotton gauze.

Gas distribution is between two thin channel layers 26/28 that are air and water tight, preferably formed from a thin, pliable plastic material, such as polyethylene. One method of manufacturing these channel layers 26/28 is by thermoforming two sheets of polyethylene to create the specific shape required (substantially rectangular is shown). By forming the channel layers 26/28 with air and water tight material, the gas entering from the input connector 11 does not permeate out through the layers 26/28, and liquids do not seep in. Furthermore, channel layers 26/28 do not absorb and hold liquids or moisture.

A spiral tube 15a is positioned between the channel layers 26/28, preferably before the layers are bonded/affixed to each other, for example, by heat, ultrasonic welding, an adhesive, etc.

In some embodiments, a bottom, comfort layer of material 24 is included to insulate the user from the material of the channel layers 26/28. In such embodiments, the bottom layer of material 24 is affixed to the bottom channel layer 26 by any way known such as by adhesive, adhesive tape, etc. Although there is no limitation on the material used for the bottom comfort layer 24, a soft cotton layer is anticipated to insulate the user's skin from the material of the bottom channel layer 26.

In some embodiments, the bandage/diaper drying system 10/10A is supported by a top layer 22 that is preferably a flexible, planar sheet of material 22 that provides additional structure to the bandage/diaper drying systems 10/10A, helping to maintain the overall shape of the bandage/diaper drying system 10/10A (rectangular shown in FIG. 4). In some embodiments, a portion or the entire top layer 22 includes an adhesive for holding the bandage/diaper drying system 10/10A to a surface of the target product (e.g. bandage, diaper). Although there is no restriction on the type of material used for the top layer 22, again, one possible material is cotton.

In FIG. 5, the bandage/diaper drying system 10/10A is shown assembled. The spiral tube 15a is visible in the inlet channel 12 because the top layer 22, in this example, does not cover the entire inlet channel 12.

Figure 6:
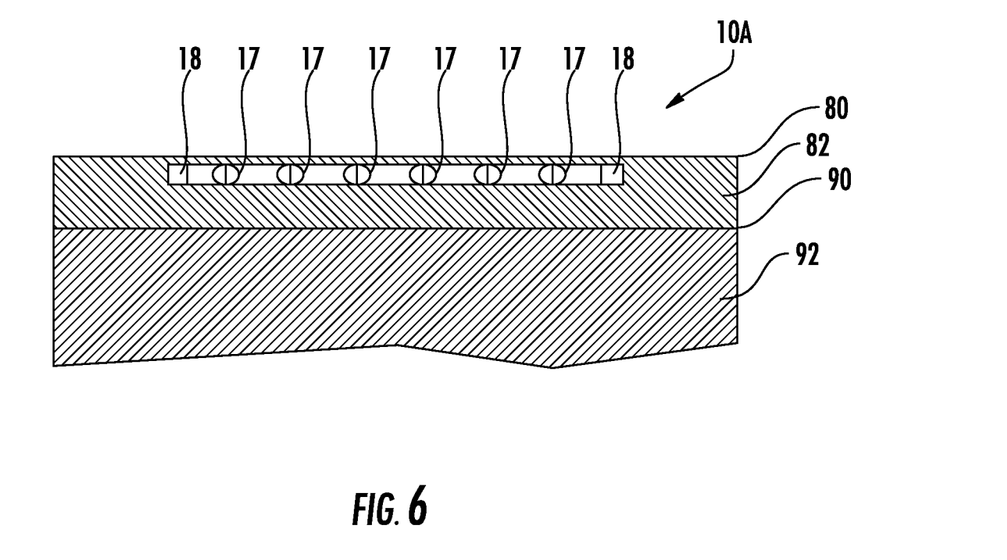
FIG. 6 illustrates a cross-sectional view of the exemplary bandage/diaper drying system inserted/installed in, for example, a diaper.

Referring to FIG. 6, a cross section view of the second exemplary bandage/diaper drying system 10/10A is shown inserted (e.g., affixed) or installed in a diaper 80/82. In this, the bandage/diaper drying system 10/10A is installed in a diaper 80/82 between the outer protective liner 80 and the absorbent core 82 (e.g. super absorbent polymers, cotton, etc.). Although shown in a pocket between the outer protective liner 80 and the absorbent core 82, there is no restriction as to where or how the bandage/diaper drying system 10A is installed/placed within the target object (e.g. diaper). For example, in some installations, the bandage/diaper drying system 10A is installed within the absorbent core 82, or, in the case of a bandage, between wrappings of a bandage, etc. For completeness, part of the epidermis 90 and tissue 92 of a user is shown.

The bandage/diaper drying system 10/10A is anticipated to be used to augment chemical therapies, as a non-medical drying device, for embedded portable localized hyperbaric oxygen (HBO) therapies, for "natural" homeopathic delivery system, embedded in an autonomous therapeutic diaper configured either with embedded DOST layer or removable/replaceable diaper liner device, as an adjunct to medical and other current care modalities. The bandage/diaper drying system 10/10A provides continuous flow of gas from the inlet connector 11 through a bendable, twistable, channel that is difficult to occlude. Drying occurs within the closed environment of the diaper/incontinence garment. Any form factor such as rectangular (shown in figures), triangular, circular, and tuning fork is anticipated.

Referring to FIG. 7, a pictorial view of a spiral tube 15a as used in embodiments of the bandage/diaper drying system is shown. Although other type of spacing members are anticipated, the spiral tube 15a is preferred to maintain air flow within the gas distribution channels 12/18 while providing a low profile and flexibility. It is anticipated that the spiral tube 15a be made of any shape-holding, but flexible material such as plastic or thin metal. The gases flow through the center bore of the spiral tube 15a and exit through the gaps between wrappings of the spiral tube 15a. As the gas escapes through the gaps between wrappings of the spiral tube 15a, the gas is directed out exit ports or vents 16 (and, in some embodiments, check valves 17) and is directed towards the area to be dried (e.g. wet are of a diaper or a wound).

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A bandage/diaper drying system comprising:
   a gas inlet;
   a gas distribution channel, the gas distribution channel in fluid communication with the gas inlet;
   a crush-resistant spacing member within the gas distribution channel; and
   a plurality of vents interfaced to the gas distribution channel, each vent in fluid communication with the gas distribution channel;
   wherein the gas distribution channel is formed from two sheets of planar material affixed to each other on opposing edges of the gas distribution channel, and the crush-resistant spacing member is a spiral tube traversing an inside length of the gas distribution channel, the spiral tube for holding the gas distribution channel open.

2. The bandage/diaper drying system of claim 1, wherein each of the vents includes a check valve, each of the check valves allows flow of gas from the gas distribution channel out of a corresponding vent and each of the check valves blocks flow of contamination into the corresponding vent and gas distribution channel.

3. The bandage/diaper drying system of claim 2, wherein the check valves are duckbill valves.

4. The bandage/diaper drying system of claim 1, wherein the gas distribution channel is substantially rectangular and the vents are interfaced to the gas distribution channel such that the vents aim inwardly.

5. The bandage/diaper drying system of claim 1, wherein each of the two sheets of planar material is a thin sheet of polyethylene.

6. The bandage/diaper drying system of claim 1, wherein the two sheets of planar material are affixed to each other by ultrasonic welding.

7. The bandage/diaper drying system of claim 1, further comprising a cloth outer layer covering the gas distribution channel.

8. The bandage/diaper drying system of claim 1, further comprising a cloth bottom layer hold a shape of the gas distribution channel.

9. The bandage/diaper drying system of claim 1, wherein the cloth bottom layer includes an adhesive for holding the cloth bottom layer to the bandage/diaper.

10. The bandage/diaper drying system of claim 1, further comprising a gas connector, the gas connector in fluid connection with the gas distribution channel and the gas connector for connecting to a source of gas.

11. A bandage/diaper drying system comprising:
    a gas inlet;
    a spiral tube;
    a gas distribution channel, the gas distribution channel in fluid communications with the gas inlet, the gas distribution channel formed around the spiral tube; and a plurality of vents interfaced to the gas distribution channel, each vent in fluid communication with the gas distribution channel and each of the vents having a check valve, each check valve allowing the flow of gas out of the a corresponding vent and reducing a flow of contaminates into the corresponding vent and the gas distribution channel.

12. The bandage/diaper drying system of claim 11, wherein the check valves are duckbill valves.

13. The bandage/diaper drying system of claim 11, wherein the gas distribution channel is formed from two sheets of planar material affixed to each other on opposing edges of the gas distribution channel, the spiral tube holding the gas distribution channel open.

14. The bandage/diaper drying system of claim 13, wherein each of the two sheets of planar material is a thin sheet of polyethylene.

15. The bandage/diaper drying system of claim 13, wherein the two sheets of planar material are affixed to each other by ultrasonic welding.

16. A bandage/diaper drying system comprising:
a gas inlet having a gas connector for connecting to a supply of gas,
an occlusion-resistant spacing member;
a gas distribution channel, the gas distribution channel in fluid communications with the gas inlet, the gas distribution channel formed around the occlusion-resistant spacing member; and
a plurality of vents interfaced to the gas distribution channel, each vent in fluid communication with the gas distribution channel and each of the vents having a duckbill check valve, each duckbill check valve allowing the flow of gas out of the gas distribution channel and reducing a flow of contaminates into the gas distribution channel;
wherein the gas distribution channel is formed from two sheets of planar material affixed to each other on opposing edges of the gas distribution channel, and the occlusion-resistant spacing member is a spiral tube holding the gas distribution channel open.

17. The bandage/diaper drying system of claim 16, wherein each of the two sheets of planar material is a thin sheet of polyethylene.

18. The bandage/diaper drying system of claim 16, wherein the two sheets of planar material are affixed to each other by ultrasonic welding.

* * * * *